United States Patent
Liu et al.

(10) Patent No.: US 12,152,069 B2
(45) Date of Patent: Nov. 26, 2024

(54) NUCLEIC ACID MOLECULES AND APPLICATIONS THEREOF IN HUMAN ANTIBODY

(71) Applicant: CHONGQING JINMAIBO BIOTEC CO., LTD, Chongqing (CN)

(72) Inventors: Zuohua Liu, Chongqing (CN); Liangpeng Ge, Chongqing (CN); Yuchun Ding, Chongqing (CN); Xiangang Zou, Chongqing (CN); Songquan Yang, Chongqing (CN); Xiaoyan You, Chongqing (CN); Xueqin Liu, Chongqing (CN); Meng Wu, Chongqing (CN)

(73) Assignee: CHONGQING JINMAIBO BIOTEC CO., LTD, Chongqing (CN)

( * ) Notice: Subject to any disclaimer, the term of this patent is extended or adjusted under 35 U.S.C. 154(b) by 1065 days.

(21) Appl. No.: 17/041,460

(22) PCT Filed: Apr. 16, 2018

(86) PCT No.: PCT/CN2018/083163
§ 371 (c)(1),
(2) Date: Sep. 25, 2020

(87) PCT Pub. No.: WO2019/184015
PCT Pub. Date: Oct. 3, 2019

(65) Prior Publication Data
US 2021/0009670 A1    Jan. 14, 2021

(30) Foreign Application Priority Data
Mar. 27, 2018 (CN) .......... 201810261091.2

(51) Int. Cl.
*C07K 16/18* (2006.01)
*A01K 67/0275* (2024.01)
*C12N 15/85* (2006.01)

(52) U.S. Cl.
CPC .......... *C07K 16/18* (2013.01); *A01K 67/0275* (2013.01); *C12N 15/85* (2013.01); *A01K 2217/052* (2013.01); *A01K 2217/15* (2013.01); *A01K 2227/105* (2013.01); *C07K 2317/21* (2013.01); *C07K 2317/24* (2013.01); *C12N 2015/8518* (2013.01)

(58) Field of Classification Search
CPC ..... C07K 16/18; A01K 67/0275; C12N 15/85
See application file for complete search history.

(56) References Cited

U.S. PATENT DOCUMENTS

| 8,629,317 B2 * | 1/2014 | Cogne | ..................... A61P 35/00 800/13 |
| 2012/0167237 A1 * | 6/2012 | Bradley | ................ A61K 39/35 800/9 |

FOREIGN PATENT DOCUMENTS

| CN | 105441455 A | 3/2016 | |
| JP | 2009532034 A | 9/2009 | |
| JP | 2012532598 A | 12/2012 | |
| WO | WO-2007117410 A2 * | 10/2007 | ......... A01K 67/0278 |

OTHER PUBLICATIONS

Pluschke et al. Generation of chimeric monoclonal antibodies from mice that carry human immunoglobulin Cg 1 heavy or Ck light chain gene segments. Journal of Immunological Methods 215: 27-37. (Year: 1998).*
Harding Class Switching in Human Immunoglobulin Transgenic Mice. Ann N Y Acad Sci 764: 536-546. (Year: 1995).*
GenBank (Mus musculus immunoglobulin heavy constant mu NC_000078.7). https://www.ncbi.nlm.nih.gov/gene/16019 (Year: 2024).*

* cited by examiner

*Primary Examiner* — Arthur S Leonard
*Assistant Examiner* — Keenan A Bates
(74) *Attorney, Agent, or Firm* — Bayramoglu Law Offices LLC

(57) ABSTRACT

Nucleic acid molecules include immunoglobulin genes or parts of immunoglobulin genes. The nucleic acid molecules includes the IgM gene (IgHCμ) and IgM switch region (Sμ). The sequences of the Sμ and the IgHCμ are both derived from a transgenic host animal. In this invention, human antibodies are directly generated and no humanization process is required, and the human antibody druggability is increased. The transgenic human antibody mouse has normal early B⁻cell development, maturation and the B⁻cell number in comparison with that of wild type animal, thereby facilitating the differentiation of the B⁻cells. The specificity and diversity of the produced antibody are improved; and the efficiency for screening the therapeutic antibody is improved.

7 Claims, 7 Drawing Sheets
Specification includes a Sequence Listing.

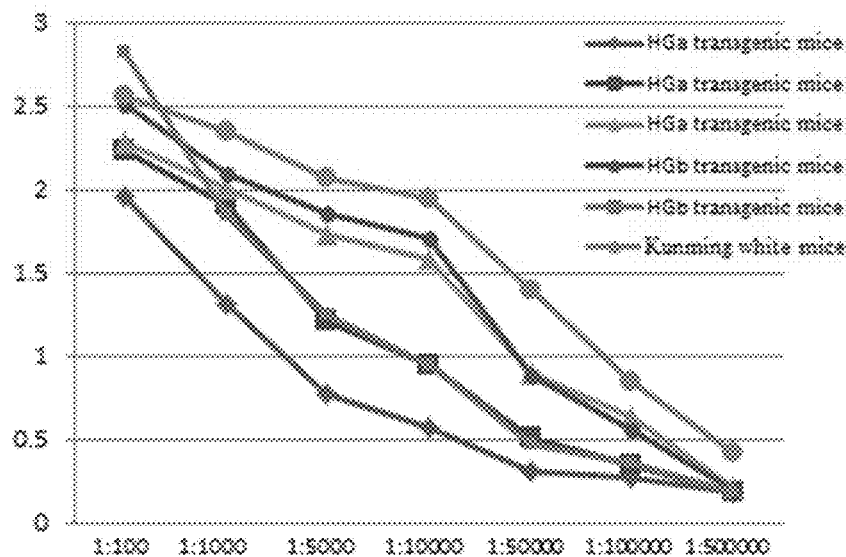
FIG. 13
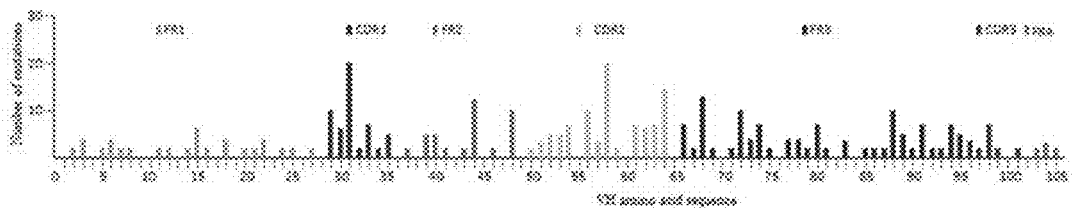
FIG. 14
| Block A | 1 | 2 | 3 | 4 | 5 | 6 | 7 | 8 | 9 | 10 | 11 | 12 |
|---|---|---|---|---|---|---|---|---|---|---|---|---|
| A | 0.057 | 0.063 | 0.06 | 0.058 | 0.06 | 0.055 | 0.059 | 0.057 | 0.059 | 0.057 | 0.065 | 0.064 |
| B | 0.079 | 0.103 | 0.091 | 1.435 | 0.695 | 0.073 | 1.127 | 0.096 | 0.081 | 0.072 | 0.103 | 0.099 |
| C | 0.056 | 0.063 | 0.066 | 0.07 | 0.055 | 1.259 | 0.692 | 0.063 | 0.058 | 0.413 | 0.069 | 0.085 |
| D | 0.056 | 0.87 | 0.745 | 0.594 | 0.061 | 0.83 | 0.07 | 0.075 | 0.068 | 1.348 | 1.014 | 0.069 |
| E | 0.077 | 0.708 | 0.088 | 1.159 | 0.626 | 1.276 | 0.876 | 0.079 | 0.091 | 0.719 | 0.987 | 0.095 |
| F | 0.088 | 0.103 | 1.378 | 1.467 | 0.601 | 1.054 | 0.089 | 1.085 | 0.722 | 0.96 | 0.607 | 0.1 |
| G | 0.078 | 0.1 | 0.643 | 0.078 | 0.082 | 0.498 | 1.723 | 0.062 | 0.378 | 0.381 | 0.077 | 0.086 |
| H | 0.081 | 0.103 | 0.092 | 0.092 | 0.08 | 0.106 | 0.105 | 0.096 | 0.086 | 0.07 | 0.071 | 0.099 |
| Block B | 1 | 2 | 3 | 4 | 5 | 6 | 7 | 8 | 9 | 10 | 11 | 12 |
|---|---|---|---|---|---|---|---|---|---|---|---|---|
| A | 0.059 | 0.083 | 0.083 | 0.057 | 0.058 | 0.062 | 0.06 | 0.057 | 0.058 | 0.058 | 0.06 | 0.068 |
| B | 0.086 | 0.117 | 0.098 | 0.091 | 0.097 | 0.11 | 1.774 | 1.541 | 0.09 | 0.488 | 0.094 | 0.102 |
| C | 0.075 | 0.077 | 0.07 | 1.479 | 0.055 | 1.487 | 0.206 | 0.069 | 0.545 | 1.804 | 0.068 | 0.081 |
| D | 0.062 | 0.071 | 0.072 | 0.054 | 0.067 | 1.636 | 0.079 | 0.085 | 0.08 | 0.071 | 1.728 | 0.094 |
| E | 0.068 | 1.466 | 0.081 | 0.079 | 0.066 | 1.621 | 1.659 | 0.088 | 0.099 | 0.08 | 1.748 | 0.1 |
| F | 0.09 | 0.121 | 0.099 | 1.756 | 0.094 | 0.105 | 1.727 | 0.127 | 0.155 | 0.091 | 0.092 | 0.115 |
| G | 0.075 | 0.106 | 0.126 | 0.074 | 0.089 | 0.106 | 0.087 | 0.08 | 0.087 | 0.094 | 0.081 | 0.1 |
| H | 0.072 | 0.078 | 0.095 | 0.085 | 0.072 | 0.118 | 0.076 | 0.111 | 0.093 | 0.085 | 0.094 | 0.08 |
FIG. 15

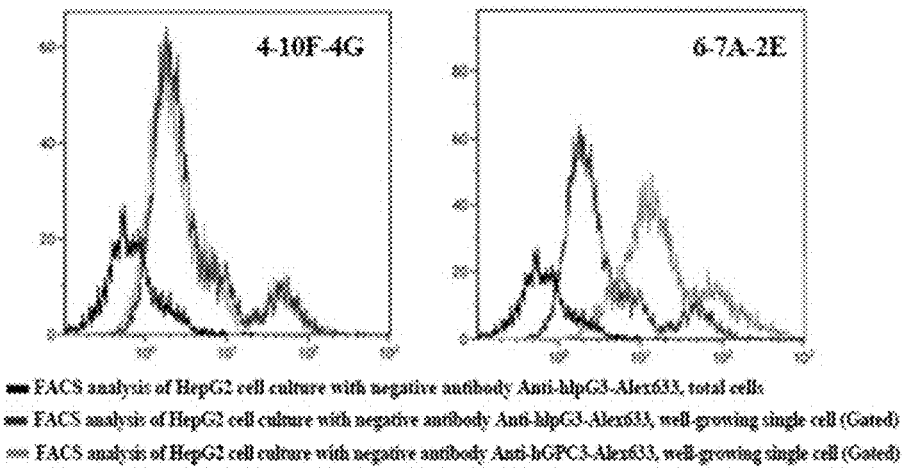

FIG. 16

| Animals | Antigen | Fusion times[a] | Hybridoma number | Human/Mouse IgG[b] | KD (nM) |
|---|---|---|---|---|---|
| HGa | OVA | 1 | 2780 | 11 | 0.3-2.6 |
| HGb | OVA | 1 | 3450 | 39 | 0.09-1.1 |
| Kunming white mouse | OVA | 1 | 6050 | 44 | 0.05-3.2 |
| HGa | GPC3 peptides/KLH | 2 | 2120 | 9 | 1.2-3.4 |
| HGb | GPC3 peptides/KLH | 2 | 3500 | 21 | 0.3-7.6 |
| Kunming white mouse | GPC3 peptides/KLH | 2 | 4830 | 25 | 0.1-4.3 |
| HGa | GPC3 protein | 1 | 3680 | 27 | 0.08-1.9 |
| HGb | GPC3 protein | 1 | 6430 | 14 | 0.1-3.6 |
| Kunming white mouse | GPC3 protein | 1 | 4500 | 25 | 0.07-2.9 | a. Serum titer of mouse Elisa (1:8000dilution), $OD_{450} > 1$;

b. HGa and HGb both can generate human IgG, and Kunming white mice generate mouse IgG, antigen-specific antibodies.

FIG. 17

SEQUENCE LISTING

```
<160> NUMBER OF SEQ ID NOS: 3

<210> SEQ ID NO 1
<211> LENGTH: 12288
<212> TYPE: DNA
<213> ORGANISM: Artificial Sequence
<220> FEATURE:
<223> OTHER INFORMATION: Mouse 5'-enhancer and IgM sequences replace
      human 5'-enhancer and IgM and IgD sequences (human and murine
      sequences and synthetic DNA)
<220> FEATURE:
<221> NAME/KEY: misc_recomb
<222> LOCATION: (1)..(8)
<223> OTHER INFORMATION: Not1 restriction site (synthetic sequence)
<220> FEATURE:
<221> NAME/KEY: misc_recomb
<222> LOCATION: (9)..(370)
<223> OTHER INFORMATION: Homology arm (human sequence)
<220> FEATURE:
<221> NAME/KEY: enhancer
<222> LOCATION: (433)..(1444)
<223> OTHER INFORMATION: Mouse IgH 5'-enhancer (mouse sequence)
<220> FEATURE:
<221> NAME/KEY: S_region
<222> LOCATION: (2550)..(4451)
<223> OTHER INFORMATION: Mouse IgM switch region (mouse sequence)
<220> FEATURE:
<221> NAME/KEY: C_region
<222> LOCATION: (5674)..(5988)
<223> OTHER INFORMATION: Mouse IgM CH1 (mouse sequence)
<220> FEATURE:
<221> NAME/KEY: C_region
<222> LOCATION: (6100)..(6438)
<223> OTHER INFORMATION: Mouse IgM CH2 (mouse sequence)
<220> FEATURE:
<221> NAME/KEY: C_region
<222> LOCATION: (6718)..(7035)
<223> OTHER INFORMATION: Mouse IgM CH3 (mouse sequence)
<220> FEATURE:
<221> NAME/KEY: C_region
```

```
<222> LOCATION: (7143)..(7537)
<223> OTHER INFORMATION: Mouse IgM CH4 (mouse sequence)
<220> FEATURE:
<221> NAME/KEY: PolyA_signal
<222> LOCATION: (7538)..(7889)
<223> OTHER INFORMATION: Mouse PolyA signal sequence (mouse sequence)
<220> FEATURE:
<221> NAME/KEY: Gene
<222> LOCATION: (9336)..(9451)
<223> OTHER INFORMATION: Mouse TM1(mouse sequence)
<220> FEATURE:
<221> NAME/KEY: Gene
<222> LOCATION: (9570)..(9575)
<223> OTHER INFORMATION: Mouse TM2(mouse sequence)
<220> FEATURE:
<221> NAME/KEY: PolyA_signal
<222> LOCATION: (9575)..(10030)
<223> OTHER INFORMATION: Mouse PolyA signal sequence (mouse sequence)
<220> FEATURE:
<221> NAME/KEY: misc_signal
<222> LOCATION: (10126)..(10159)
<223> OTHER INFORMATION: Lox (synthetic sequence)
<220> FEATURE:
<221> NAME/KEY: misc_signal
<222> LOCATION: (10160)..(10322)
<223> OTHER INFORMATION: pGK-Puromycin screening gene (synthetic
      sequence)
<220> FEATURE:
<221> NAME/KEY: misc_signal
<222> LOCATION: (11482)..(11515)
<223> OTHER INFORMATION: Lox (synthetic sequence)
<220> FEATURE:
<221> NAME/KEY: misc_recomb
<222> LOCATION: (11516)..(11797)
<223> OTHER INFORMATION: Homology arm (mouse sequence)
<220> FEATURE:
<221> NAME/KEY: misc_recomb
<222> LOCATION: (11798)..(11805)
<223> OTHER INFORMATION: AsiS1 (synthetic sequence)
<220> FEATURE:
<221> NAME/KEY: misc_recomb
<222> LOCATION: (11806)..(12280)
<223> OTHER INFORMATION: Homology arm (human sequence)
<220> FEATURE:
<221> NAME/KEY: misc_recomb
<222> LOCATION: (12281)..(12288)
<223> OTHER INFORMATION: Not1 restriction site (synthetic sequence)

<400> SEQUENCE: 1
gcggccgccg agatgcctga acaaaccagg ggtcttagtg atggctgagg aatgtgtctc      60
aggagcggtg tctgtaggac tgcaagatcg ctgcacagca gcgaatcgtg aaatattttc     120
tttagaatta tgaggtgcgc tgtgtgtcaa cctgcatctt aaattcttta ttggctggaa     180
agagaactgt cggagtgggt gaatccagcc aggagggacg cgtagccccg gtcttgatga     240
gagcagggtt gggggcaggg gtagcccaga aacggtggct gccgtcctga caggggctta     300
gggaggctcc aggacctcag tgccttgaag ctggtttcca agagaaaagg attgtttatc     360
ttaggaggca tcttagtgat tgagtcaagg gagaaaggca tctagcctcg gtctcaaaag     420
ggtagttgct gtctagagag gtctggtgga gcctgcaaaa gtccagcttt caaaggaaca     480
cagaagtatg tgtatggaat attagaagat gttgctttta ctcttaagtt ggttcctagg     540
aaaaatagtt aaatactgtg actttaaaat gtgagagggt tttcaagtac tcatttttt      600 aaatgtccaa aattcttgtc aatcagtttg aggtcttgtt tgtgtagaac tgatattact     660
taaagtttaa ccgaggaatg ggagtgaggc tctctcataa cctattcaga actgactttt     720
aacaataata aattaagttt caaatatttt taaatgaatt gagcaatgtt gagttggagt     780
caagatggcc gatcagaacc agaacacctg cagcagctgg caggaagcag gtcatgtggc     840
aaggctattt ggggaaggga aaataaaacc actaggtaaa cttgtagctg tggtttgaag     900
```

```
aagtggtttt gaaacactct gtccagcccc accaaaccga aagtccaggc tgagcaaaac    960
accacctggg taatttgcat ttctaaaata agttgaggat tcagccgaaa ctggagaggt   1020
cctcttttaa cttattgagt tcaacctttt aattttagct tgagtagttc tagtttcccc   1080
aaacttaagt ttatcgactt ctaaaatgta tttagaattc attttcaaaa ttaggttatg   1140
taagaaattg aaggacttta gtgtctttaa tttctaatat atttagaaaa cttcttaaaa   1200
ttactctatt attcttccct ctgattattg gtctccattc aattcttttc caatacccga   1260
agcatttaca gtgactttgt tcatgatctt ttttagttgt ttgttttgcc ttactattaa   1320
gactttgaca ttctggtcaa aacggcttca caaatctttt tcaagaccac tttctgagta   1380
ttcattttag gagaaagact tttttttttaa atgaatgcaa ttatctagac ttatttcagt   1440
tgaacatgct ggttggtggt tgagaggaca ctcagtcagt cagtgacgtg aagggcttct   1500
aagccagtcc acatgctctg tgtgaactcc ctctggccct gcttattgtt gaatgggcca   1560
aaggtctgag accaggctgc tgctgggtag gcctggactt tgggtctccc acccagacct   1620
gggaatgtat ggttgtggct tctgccaccc atccacctgg ctgctcatgg accagccagc   1680
ctcggtggct ttgaaggaac aattccacac aaagactctg gacctctccg aaaccaggca   1740
ccgcaaatgg taagccagag gcagccacag ctgtggctgc tgctcttaaa gcttgtaaac   1800
tgtttctgct taagagggac tgagtcttca gtcattgctt tagggggaga aagagacatt   1860
tgtgtgtctt ttgagtaccg ttgtctgggt cactcacatt taactttcct tgaaaaacta   1920
gtaaaagaaa aatgttgcct gttaaccaat aatcatagag ctcatggtac tttgaggaaa   1980
tcttagaaag cgtgtataca attgtctgga attatttcag ttaagtgtat tagttgaggt   2040
actgatgctg tctctacttc agttatacat gtgggtttga attttgaatc tattctggct   2100
cttcttaagc agaaaattta gataaaatgg atacctcagt ggttttttaat ggtgggttta   2160 atatagaagg aatttaaatt ggaagctaat ttagaatcag taaggaggga cccaggctaa   2220
gaaggcaatc ctgggattct ggaagaaaag atgttttttag ttttttataga aaacactact   2280 acattcttga tctacaactc aatgtggttt aatgaatttg aagttgccag taaatgtact   2340
tcctggttgt taaagaatgg tatcaaagga cagtgcttag atccgaggtg agtgtgagag   2400
gacaggggct ggggtatgga tacgcagaag gaaggccaca gctgtacaga attgagaaag   2460
aatagagacc tgcagttgag gccagcaggt cggctggact aactctccag ccacagtaat   2520
gacccagaca gagaaagcca gactcataaa gcttgctgag caaaattaag ggaacaaggt   2580
tgagagccct agtaagcgag gctctaaaaa gcacagctga gctgagatgg gtgggcttct   2640
ctgagtgctt ctaaaatgcg ctaaactgag gtgattactc tgaggtaagc aaagctgggc   2700
ttgagccaaa atgaagtaga ctgtaatgaa ctggaatgag ctgggccgct aagctaaact   2760
aggctggctt aaccgagatg agccaaactg gaatgaactt cattaatcta ggttgaatag   2820
agctaaactc tactgcctac actggactgt tctgagctga gatgagctgg ggtgagctca   2880
gctatgctac gctgtgttgg ggtgagctga tctgaaatga gatactctgg agtagctgag   2940
atggggtgag atggggtgag ctgagctggg ctgagctaga ctgagctgag ctagggtgag   3000
ctgagctggg tgagctgagc taagctgggg tgagctgagc tgagcttggc tgagctaggg   3060
tgagctgggc tgagctgggg tgagctgagc tgagctgggg taagctggga tgagctgggg   3120
tgagctgagc tgagctggag tgagctgagc tgggctgagc tggggtgagc tgggctgagc   3180
tgggctgagc tgggctgagc tggggtgagc tgagctgggg tgagctgagc tgagctgggg   3240
```

```
tgagctgagc tgagctgggg tgagctgggg tgagctgagc tggggtgagc tgagctgagc      3300
tggggtgagc tgagctgggg tgagctgagc tgagctgggg tgagctgagc tgagctgagc      3360
tgagctgagc tggggtgagc tgagctgagc tgagctgggg tgagctgggg tgagctgagc      3420
tgagctggag tgagctgagc tgggctgagc tggggtgagc tgggctgagc tggggtgagc      3480
tgagctgagc tgagctgagc tggggtgagc tgagctgagc tggggtgagc tgagctgggg      3540
tgagctgggc tgagctgagc tgagctgagc tgagctgagc tgagctgagc tgagctgagc      3600
tgagctgagc tgagctgagc tgagctgagc tgagctgagc tgagctgggg tgagctgagc tgagctgggc  3660
tgagctgggg tgagctgggc tgagctgggc tgagctgggc tgagctggggg tgagctgagc     3720 tggggtgagc tgagctgagc tgggctgagc tgagctgagc tggggtgagc tgagctgagc      3780
tggggtgagc tgagctgagc tgagctgggg tgagctgagc tgggctgagc agggctgagc      3840
tggggtgagc tgagctgagc tggggtgagc tgggctgagc tgggctgagc tgagctgagc      3900
tgggctgagc tgggctgagc tgggctgagc tgggctgagc tgggctgagc tggggtgagc      3960
tgagctgagc tggggtgagc tggggtgagc tgagctgggg tgagctgagc tggggtgagc      4020
tgagctgagc tggggtgagc tgagctgggg tgagctgagc tgagctgggg tgagctgagc      4080
tgagctgggg tgagctgagc tagggtgaac tgggctgggt gagctggagt gagctgagct      4140
gaggtgaact ggggtgagcc gggatgtttt gagttgagct ggggtaagat gagctgaact      4200
ggggtaaact gggatgagct gtggtgagcg gagctggatt gaactgagct gtgtgagctg      4260
agctggggtc agctgagcaa gagtgagtag agctggctgg ccagaaccag aatcaattag      4320
gctaagtgag ccagattgtg ctgggatcag ctgtactcag atgagctggg atgaggtagg      4380
ctgggatgag ctgggctagc tgacatggat tatgtgaggc tgagctagca tgggctggcc      4440
tagctgatga gctaagcttg aatgagcggg gctgagctgg actcagatgt gctagactga      4500
gctgtactgg atgatctggt gtagggtgat ctggactcaa ctgggctggc tgatgggatg      4560
cgccaggttg aactaggctc agataagtta ggctgagtag ggcctggttg agatggttcg      4620
ggatgagctg ggaaaagatg gactcggacc atgaactggg ctgagctggg ttgggagacc      4680
atgaattgag ctgaactgag tgcagctggg ataaactggg ttgagctaag aatagactac      4740
ctgaattgtg ccaaactcgg ctgggatcaa ttggaaatta tcaggattta gatgagccgg      4800
actaaactat gctgagctgg actggttgga tgtgttgaac tggcctgctg ctgggctggc      4860
atagctgagt tgaacttaaa tgaggaaggc tgagcaaggc tagcctgctt gcatagagct      4920
gaactttagc ctagcctgag ctggaccagc ctgagctgag taggtctaaa ctgagttaaa      4980
aatcaacagg ataatttaa cagctaattt aacaagcctg aggtctgaga ttgaatgagc      5040
agagctggga tgaactgaat gagtttcacc aggcctggac cagttaggct aggacctcgt      5100
tctatagagg cagactgtgt gctacagtgg agtttcaaga tgattccatg agtcctcccc      5160
gcccccaaca taacccacct tcctcctacc ctacacgcct gtctggtgtg taaatcccag      5220
ctttgtgtgc tgatacagaa gcctgagccc ctcccccacc tccacctacc tattactttg      5280
ggatgagaat agttctccca gccagtgtct cagagggaag ccaagcagga caggcccaag      5340
gctacttgag aagccaggat ctaggcctct ccctgagaac gggtgttcat gcccctagag      5400
ttggctgaag ggccagatcc acctactcta gaggcatctc tccctgtctg tgaaggcttc      5460
caaagtcacg ttcctgtggc tagaaggcag ctccatagcc ctgctgcagt ttcgtcctgt      5520
ataccaggtt cacctactac catatctagc cctgcctgcc ttaagagtag caacaaggaa      5580
atagcagggt gtagagggat ctcctgtctg acaggaggca agaagacaga ttcttacccc      5640
```

```
tccatttctc ttttatccct ctctggtcct cagagagtca gtccttccca aatgtcttcc    5700
ccctcgtctc ctgcgagagc cccctgtctg ataagaatct ggtggccatg ggctgcctgg    5760
cccgggactt cctgcccagc accatttcct tcacctggaa ctaccagaac aacactgaag    5820
tcatccaggg tatcagaacc ttcccaacac tgaggacagg gggcaagtac ctagccacct    5880
cgcaggtgtt gctgtctccc aagagcatcc ttgaaggttc agatgaatac ctggtatgca    5940
aaatccacta cggaggcaaa aacaaagatc tgcatgtgcc cattccaggt aagaaccaaa    6000
ccctcccagc aggggtgccc aggcccaggc atggcccaga gggagcagcg gggtggggct    6060
taggccaagc tgagctcaca ccttgacctt tcattccagc tgtcgcagag atgaacccca    6120
atgtaaatgt gttcgtccca ccacgggatg gcttctctgg ccctgcacca cgcaagtcta    6180
aactcatctg cgaggccacg aacttcactc caaaaccgat cacagtatcc tggctaaagg    6240
atgggaagct cgtggaatct ggcttcacca cagatccggt gaccatcgag aacaaaggat    6300
ccacacccca aacctacaag gtcataagca cacttaccat ctctgaaatc gactggctga    6360
acctgaatgt gtacacctgc cgtgtggatc acagggggtct caccttcttg aagaacgtgt    6420
cctccacatg tgctgccagt gagtggcctg ggctaagccc aatgcctagc cctcccagat    6480
tagggaagtc ctcctacaat tatggccaat gccacccaga catggtcatt tgctccttga    6540
actttggctc cccagagtgg ccaaggacaa gaatgagcaa taggcagtag aggggtgaga    6600
atcagctgga aggaccagca tcttccctta agtaggtttg ggggatggag actaagcttt    6660
tttccaactt cacaactaga tatgtcataa cctgacacag tgttctcttg actgcaggtc    6720
cctccacaga catcctaacc ttcaccatcc cccctcctt tgccgacatc ttcctcagca    6780
agtccgctaa cctgacctgt ctggtctcaa acctggcaac ctatgaaacc ctgaatatct    6840
cctgggcttc tcaaagtggt gaaccactgg aaaccaaaat taaaatcatg gaaagccatc    6900
ccaatggcac cttcagtgct aagggtgtgg ctagtgtttg tgtggaagac tggaataaca    6960
ggaaggaatt tgtgtgtact gtgactcaca gggatctgcc ttcaccacag aagaaattca    7020
tctcaaaacc caatggtagg tatcccccct tcccttcccc tccaattgca ggacccttcc    7080
tgtacctcat agggagggca ggtcctcttc caccctatcc tcactactgt cttcatttac    7140
agaggtgcac aaacatccac ctgctgtgta cctgctgcca ccagctcgtg agcaactgaa    7200
cctgagggag tcagccacag tcacctgcct ggtgaagggc ttctctcctg cagacatcag    7260
tgtgcagtgg cttcagagag ggcaactctt gccccaagag aagtatgtga ccagtgcccc    7320
gatgccagag cctggggccc caggcttcta ctttacccac agcatcctga ctgtgacaga    7380
ggaggaatgg aactccggag agacctatac ctgtgttgta ggccacgagg ccctgccaca    7440
cctggtgacc gagaggaccg tggacaagtc cactggtaaa cccacactgt acaatgtctc    7500
cctgatcatg tctgacacag gcggcacctg ctattgacca tgctagcgct caaccaggca    7560
ggccctgggt gtccagttgc tctgtgtatg caaactaacc atgtcagagt gagatgttgc    7620
attttataaa aattagaaat aaaaaaaatc cattcaaacg tcactggttt tgattataca    7680
atgctcatgc ctgctgagac agttgtgttt tgcttgctct gcacacaccc tgcatacttg    7740
cctccaccct ggcccttcct ctaccttgcc agtttcctcc ttgtgtgtga actcagtcag    7800
gcttacaaca gacagagtat gaacatgcga ttcctccagc tacttctaga tatatggctg    7860
aaagcttgcc taacctggtg caggcagcat tcaggcacat atatagacac acatgcattt    7920
atacatagat atataggtac acatgtgtag acacatacat gaatgtgtat tcatggacac    7980
```

```
acagacaaag gtacacatat atacacatga gttcatgcgc acacacatgc atggacactt    8040
acaaacgcct tcagagacaa ataggcatag acacacaacc actcacagaa acagatacca    8100
atatgcatgg tcctgtgtac acagaaacag actataggca aatatacaca aataaactat    8160
atagatacaa agatatgcat atacacacat gtacagaaac atcttcacat gtgtacacta    8220
acatgtgaac aggtatagca cacagataca cctggactct gaccagggct gtaatctcca    8280
aggctcacgg ctcagagagc ctacactagg ctgggtcact gatactcctc aggagcccac    8340
tctatgattg ggagagataa ccccaggtac aaagtatgcc tatctgtctc aacaccatgg    8400
ggcagaagat actccactaa ccacccatga cagaaagtta gccttggctg tgtctccatt    8460
aatagaacac ctcagaagac caatgtgaaa ttgcctaacc cactcacacc caccctgatc    8520
tccagttcaa aatgcagaaa acataatgca gttgtccaaa agatgcccca accacacaca    8580
cacacacaca cacacacaca cacacacaca cacacacaca cacacacaca caccatcaag    8640
gagcctctgt aaggagtcac cacccaataa cactgcctct ttgggctcat atcctggaca    8700
ttcttcatat tcatatccat ttggggccta ggctttagat atcccaaagg gctcatcttt    8760
acagggatca gagatcccaa taaatgccct ggtcccacag cctccctcag gtatctgtct    8820
gtttatctct tggtaccaag acccaacatt gctggcaggg gtaggacaag caacgcacgg    8880
gaactctgat caaagaaagt catgagatgc ctgagtcctt caggaagtaa ggagggacaa    8940
cctctggtat ccctgttctt attgctaaag cccaagagac agggagacct gctctaaatt    9000
ctcagtctaa acagcaccga tggcaccacc tgctcaggga aagtccagag cacaccaata    9060
tcattttgcc acagttcctg agtctgcctt tacccaggtc catacattgc atctgtcttg    9120
cttgctctgc tgccccaggg ctcctggaac aaaggctcca aattagtgtg tcctacagct    9180
tggcctgttc tgtgcctccg tctagcttga gctattaggg gaccagtcaa tactcgctaa    9240
gattctccag aaccatcagg gcaccccaac ccttatgcaa atgctcagtc accccaagac    9300
ttggcttgac cctccctctc tgtgtccctt catagagggg gaggtgaatg ctgaggagga    9360
aggctttgag aacctgtgga ccactgcctc caccttcatc gtcctcttcc tcctgagcct    9420
cttctacagc accaccgtca ccctgttcaa ggtagtgtgg ttgtggggct gaggacacag    9480
ggctgggaca gggagtcacc agtcctcact gcctctacct ctactcccta caagtggaca    9540
gcaattcaca ctgtctctgt cacctgcagg tgaaatgact ctcagcatgg aaggacagca    9600
gagaccaaga gatcctccca cagggacact acctctgggc ctgggatacc tgactgtatg    9660
actagtaaac ttattcttac gtcttttcctg tgttgccctc cagcttttat ctctgagatg    9720
gtcttctttc tagactgacc aaagactttt tgtcaacttg tacaatctga agcaatgtct    9780
ggcccacaga cagctgagct gtaaacaaat gtcacatgga aataaatact ttatcttgtg    9840
aactcacttt attgtgaagg aatttgtttt gttttttcaaa cctttcctgc ggtgttgaca    9900
gcccaaggat tatctgaata gagcttagga actggaaatg gaacagtgca gtctgatggt    9960
acttaaggga gaaagaggga aaggaggtgt ggaagaagaa aaaagagaag cagaggggga   10020
ggggagaagg gagagggaga gggagaggga gagggagagg gagagggaga gggagagaga   10080
gagagagaga gagagagaga gagagagaga gagagagcat gcactataac ttcgtataat   10140
gtatgctata cgaagttatc taccgggtag gggaggcgct tttcccaagg cagtctggag   10200
catgcgcttt agcagccccg ctgggcactt ggcgctacac aagtggcctc tggctcgcac   10260
acattccaca tccaccggta ggcgccaacc ggctccgttc tttggtggcc ccttcgcgcc   10320
accttctact cctcccctag tcaggaagtt ccccccccgcc ccgcagctcg cgtcgtgcag   10380
```

```
gacgtgacaa atggaagtag cacgtctcac tagtctcgtg cagatggaca gcaccgctga   10440
gcaatggaag cgggtaggcc tttggggcag cggccaatag cagctttgct ccttcgcttt   10500
ctgggctcag aggctgggaa ggggtgggtc cggggcggg ctcaggggcg ggctcagggg    10560
cggggcgggc gcccgaaggt cctccggagg cccggcattc tgcacgcttc aaaagcgcac   10620
gtctgccgcg ctgttctcct cttcctcatc tccgggcctt tcgacctgca gcagcacgtg   10680
ttgacaatta atcatcggca tagtatatcg gcatagtata atacgacaag gtgaggaact   10740
aaaccatgac cgagtacaag cccacggtgc gcctcgccac ccgcgacgac gtccccgggg   10800
ccgtacgcac cctcgccgcc gcgttcgccg actaccccgc cacgcgccac accgtcgacc   10860
cggaccgcca catcgagcgg gtcaccgagc tgcaagaact cttcctcacg cgcgtcgggc   10920
tcgacatcgg caaggtgtgg gtcgcggacg acggcgccgc ggtggcggtc tggaccacgc   10980
cggagagcgt cgaagcgggg gcggtgttcg ccgagatcgg cccgcgcatg gccgagttga   11040
gcggttcccg gctggccgcg cagcaacaga tggaaggcct cctggcgccg caccggccca   11100
aggagcccgc gtggttcctg gccaccgtcg gcgtctcgcc cgaccaccag ggcaagggtc   11160
tgggcagcgc cgtcgtgctc cccggagtgg aggcggccga gcgcgccggg gtgcccgcct   11220
tcctggagac ctccgcgccc cgcaacctcc ccttctacga gcggctcggc ttcaccgtca   11280
ccgccgacgt cgaggtgccc gaaggaccgc gcacctggtg catgacccgc aagcccggtg   11340
cctgagcggg actctggggt tcgaataaag accgaccaag cgacgtctga gagctccctg   11400
gcgaattcgg taccaataaa agagctttat tttcatgatc tgtgtgttgg tttttgtgtg   11460
cggcgcgccg tttaaacgcg gataacttcg tataatgtat gctatacgaa gttattctga   11520
ctgatctgtc catttgtgag agtagagtgt tgaagtctcc cactattaat ataatgggtt   11580
ctatgtatac tttagtaatg ttgcctttat gaatgtgggc gccatggcac ttggggcata   11640
gatgttcaga actgagaagt tatcttggtg gttttttccc tttgataagt atgaagaata   11700
cctatctctt tttattactt tcagttgaaa gtccatttta ttagatatta gaatggctac   11760
tccatgttgt ttcttgggtt catttgcttg taaatccgcg atcgccagcc tccagaatgg   11820
tgggaaataa gtttctgttg tttctcagcc accacgtctg tagtatgtgg aagtcatcag   11880
aatcaaaatt gagtcacctg tggttttttt tttttctaaa tccctgacaa atagagccta   11940
ggaaggccaa gaagagaaga gggttctcat ccataaacac ttgataacaa aaactatcac   12000
caaggactct acaaaaactg caactggcac aaagaccatc acaaccttac acagaaagta   12060
cttctgtgag gacatcttcc cagcaacggg ctgtccaacc tcagactggc attgcctttg   12120
ttattggtcc ttgtagagag ggtaattatc tcaaagcaat catgtaatcc tcctcatttt   12180 tccttttgaaa gccttggtct ccctttgcct ccctgaatac gcacatagct gatcatggca   12240
ggtgtatccc actgcagtgc tctacctcca aatagatatc gcggccgc                12288
```

<210> SEQ ID NO 2
<211> LENGTH: 2943
<212> TYPE: DNA
<213> ORGANISM: Artificial Sequence
<220> FEATURE:
<223> OTHER INFORMATION: Sequences of human IgG heavy chain (subtype 3)
      (CH1, Hinge, CH2, CH3), and mouse IgG heavy chain (subtype 3)
      homology arms [human and mouse DNA sequences (SwaI digested
      fragments)]
<220> FEATURE:
<221> NAME/KEY: misc_recomb
<222> LOCATION: (1)..(345)
<223> OTHER INFORMATION: Homology arm (mouse sequence)

```
<220> FEATURE:
<221> NAME/KEY: C_region
<222> LOCATION: (346)..(639)
<223> OTHER INFORMATION: Human IgG (subtype 3) CH1 (human sequence)
<220> FEATURE:
<221> NAME/KEY: J_segment
<222> LOCATION: (1032)..(1082)
<223> OTHER INFORMATION: Human IgG (subtype 3) Hinge (human sequence)
<220> FEATURE:
<221> NAME/KEY: C_region
<222> LOCATION: (1765)..(2094)
<223> OTHER INFORMATION: Human IgG (subtype 3) CH2 (human sequence)
<220> FEATURE:
<221> NAME/KEY: C_region
<222> LOCATION: (2194)..(2514)
<223> OTHER INFORMATION: Human IgG (subtype 3) CH3 (human sequence)
<220> FEATURE:
<221> NAME/KEY: misc_recomb
<222> LOCATION: (2515)..(2943)
<223> OTHER INFORMATION: Homology arm (Mouse sequence)

<400> SEQUENCE: 2
aaatgaaggc ttcattgagg ggaaacatga atgatgtcta cagcttcaag cacaggtgca        60
agagactata gaacagtaca tacaaaccag ctttctgaaa atatgttcag gatagagctg       120
ggctcagaaa ttctactgat caaacctagc tggtaattct ggggtggaga gggtgtaagg       180
tgaggcaatt ggaaccatca aggttgctat atgatgccct gacctaggtg atatatccta       240
catgctcttt gcagaaccct ggcatccttg taggaccaag gctgaactcc tccaggtgcc       300
tgaatccagc tgtctgataa cctcactcat cctcctatct tgcagcttcc accaagggcc       360
catcggtctt ccccctggcg ccctgctcca ggagcacctc tgggggcaca gcggccctgg       420
gctgcctggt caaggactac ttcccagaac cggtgacggt gtcgtggaac tcaggcgccc       480
tgaccagcgg cgtgcacacc ttcccggctg tcctacagtc ctcaggactc tactccctca       540
gcagcgtggt gaccgtgccc tccagcagct tgggcaccca gacctacacc tgcaacgtga       600
atcacaagcc cagcaacacc aaggtggaca agagagttgg tgagaggcca gcgcagggag       660
ggagggtgtc tgctggaagc caggctcagc cctcctgcct ggacgcatcc ggctgtgca       720 gtcccagccc agggcaccaa ggcaggcccc gtctgactcc tcacccggag gcctctgccc       780
gccccactca tgctcaggga gagggtcttc tggcttttc caccaggctc cgggcaggca       840
caggctggat gcccctaccc caggcccttc acacacaggg gcaggtgctg cgctcagagc       900
tgccaagagc catatccagg aggaccctgc ccctgaccta gcccacccc aaaggccaaa       960 ctctctactc actcagctca gataccttct ctcttcccag atctgagtaa ctcccaatct      1020
tctctctgca gagctcaaaa ccccacttgg tgacacaact cacacatgcc cacggtgccc      1080
aggtaagcca gcccaggcct cgccctccag ctcaaggcgg gacaagagcc ctagagtggc      1140
ctgagtccag ggacaggccc cagcagggt ctgacgcatc cacctccatc ccagatcccc      1200
gtaactccca atcttctctc tgcagagccc aaatcttgtg acacacctcc cccgtgccca      1260
cggtgcccag gtaagccagc ccaggcctcg ccctccagct caaggcagga caagagccct      1320
agagtggcct gagtccaggg acaggcccca gcagggtgct gacgcgtcca cctccatccc      1380
agatccccgt aactcccaat cttctctctg cagagcccaa atcttgtgac acacctcccc      1440
catgcccacg gtgcccaggt aagccagccc aggcctcgcc ctccagctca aggcgggaca      1500
agagccctag agtggcctga gtccagggac aggccccagc agggtgctga cgcatccacc      1560
tccatcccag atcccgtaa ctcccaatct tctctctgca gagcccaaat cttgtgacac      1620
acctcccccg tgcccaaggt gcccaggtaa gccagcccag gcctcgccct ccagctcaag      1680
```

```
gcaggacagg tgccctagag tggcctgcat ccagggacag gtcccagtcg ggtgctgaca    1740
catctgcctc catctcttcc tcagcacctg aactcctggg aggaccgtca gtcttcctct    1800 tcccccaaa  acccaaggat acccttatga tttcccggac ccctgaggtc acgtgcgtgg    1860
tggtggacgt gagccacgaa gaccccgagg tccagttcaa gtggtacgtg gacggcgtgg    1920
aggtgcataa tgccaagaca aagccgcggg aggagcagta caacagcacg ttccgtgtgg    1980
tcagcgtcct caccgtcctg caccaggact ggctgaacgg caaggagtac aagtgcaagg    2040
tctccaacaa agccctccca gcccccatcg agaaaaccat ctccaaaacc aaaggtggga    2100
cccgcggggt atgagggcca catggacaga ggccagcttg acccaccctc tgccctggga    2160
gtgaccgctg tgccaacctc tgtccctaca ggacagcccc gagaaccaca ggtgtacacc    2220
ctgcccccat cccgggagga gatgaccaag aaccaggtca gcctgacctg cctggtcaaa    2280
ggcttctacc ccagcgacat cgccgtggag tgggagagca cgggcagcc  ggagaacaac    2340 tacaacacca cgcctcccat gctggactcc gacggctcct tcttcctcta cagcaagctc    2400
accgtggaca agagcaggtg gcagcagggg aacatcttct catgctccgt gatgcatgag    2460
gctctgcaca accgcttcac gcagaagagc ctctccctgt ctccgggtaa atgagaacag    2520
cacctagcca ttcctcgggt cttacaagac actgatacca gccctaaccg gtgaacccta    2580
taaataaagc acccagagat gggaccttgt gagattatct tggttcttta catggcacat    2640
agttcatgat acacctcagc cacaggctgt ggggtctggc cagggttcaa ggtgtaagtt    2700
aacatccaag aaagaacaag gtcttatact gccagaccca gggcatgcaa gtggacctgc    2760
ccttgccaga gatcatccct ctctgcatag caagtttgac ccaaggggcc ctcttcatac    2820
tcttccccac aaccagcaac tgttctgtga tgagtctgga gatagaaata tcgccctaga    2880
aaatatccaa agaaaggaac acagaaagtg tatcccacct caacacgaac cccaccttca    2940
ttt                                                                 2943
```

```
<210> SEQ ID NO 3
<211> LENGTH: 2546
<212> TYPE: DNA
<213> ORGANISM: Artificial Sequence
<220> FEATURE:
<223> OTHER INFORMATION: Sequences of human IgG heavy chain (subtype 1)
      (CH1, Hinge, CH2, CH3), and mouse IgG heavy chain (subtype 1)
      homology arms [human and mouse DNA sequences (SwaI digested
      fragments)]
<220> FEATURE:
<221> NAME/KEY: misc_recomb
<222> LOCATION: (1)..(692)
<223> OTHER INFORMATION: Homology arm (mouse sequence)
<220> FEATURE:
<221> NAME/KEY: C_region
<222> LOCATION: (693)..(986)
<223> OTHER INFORMATION: Human IgG (subtype 1) CH1 (human sequence)
<220> FEATURE:
<221> NAME/KEY: J_segment
<222> LOCATION: (1378)..(1422)
<223> OTHER INFORMATION: Human IgG (subtype 1) Hinge (human sequence)
<220> FEATURE:
<221> NAME/KEY: C_region
<222> LOCATION: (1541)..(1871)
<223> OTHER INFORMATION: Human IgG (subtype 1) CH2 (human sequence)
<220> FEATURE:
<221> NAME/KEY: C_region
<222> LOCATION: (1968)..(2290)
<223> OTHER INFORMATION: Human IgG (subtype 1) CH3 (human sequence)
<220> FEATURE:
<221> NAME/KEY: misc_recomb
<222> LOCATION: (2291)..(2546)
<223> OTHER INFORMATION: Homology arm (mouse sequence)
```

```
<400> SEQUENCE: 3
aaatagttat gtcaaaccac atgtttagga gcctgggttg acttcatagg gagtaggcat         60
ggaggctaat ctagaggttt gtgtataggc aagaagtgaa tcctgaccca agaatagaga        120
gtgctaaacg gacttagttc aaagacaact gaaaaagaca atgcctgcaa aacaaagcta        180
aggccagagc tcttggacta tgaagagttc agggaaccta agaacaggga ccatctgtgt        240
acaggccaag gccggtagaa gcagcctagg aagtgtcaag agccaacgtg ctgggtggg         300 caaagacagg aagggactgt taggctgcag ggatgtgccg acttcaatgt gcttcagtat        360
tgtccagatt gtgtgcagcc atatggccca ggtataagag gtttaacagt ggaacacaga        420
tgcccacatc agacagctgg ggggcgggg tgaacacaga tacccatact ggaaagcagg         480
tggggcattt tcctaggaac gggactgggc tcaatggcct caggtctcat ctggtctggt        540
gatcctgaca ttgataggcc caaatgttgg atatcaccta ctccatgtag agagtcgggg       600
acatgggaag ggtgcaaaag agcggccttc tagaaggttt ggtcctgtcc tgtcctgtct        660
gacagtgtaa tcacatatac ttttttcttgt agcctccacc aagggcccat cggtcttccc      720
cctggcaccc tcctccaaga gcacctctgg gggcacagca gccctgggct gcctggtcaa        780
ggactacttc cccgaaccgg tgacggtgtc gtggaactca ggcgccctga ccagcggcgt       840
gcacaccttc ccggctgtcc tacagtcctc aggactctac tccctcagca gcgtggtgac        900
cgtgccctcc agcagcttgg gcacccagac ctacatctgc aacgtgaatc acaagcccag        960
caacaccaag gtggacaaga agttggtga gaggccagca cagggaggga gggtgtctgc       1020
tggaagccag gctcagcgct cctgcctgga cgcatcccgg ctatgcagcc ccagtccagg       1080
gcagcaaggc aggccccgtc tgcctcttca cccggaggcc tctgcccgcc ccactcatgc       1140
tcagggagag ggtcttctgg cttttcccc aggctctggg caggcacagg ctaggtgccc       1200
ctaacccagg ccctgcacac aaaggggcag gtgctgggct cagacctgcc aagagccata       1260
tccgggagga ccctgcccct gacctaagcc caccccaaag gccaaactct ccactccctc       1320
agctcggaca ccttctctcc tcccagattc cagtaactcc caatcttctc tctgcagagc       1380
ccaaatcttg tgacaaaact cacacatgcc caccgtgccc aggtaagcca gcccaggcct       1440
cgccctccag ctcaaggcgg gacaggtgcc ctagagtagc ctgcatccag ggacaggccc       1500
cagccgggtg ctgacacgtc cacctccatc tcttcctcag cacctgaact cctggggga        1560 ccgtcagtct tcctcttccc cccaaaaccc aaggacaccc tcatgatctc ccggacccct       1620
gaggtcacat gcgtggtggt ggacgtgagc cacgaagacc ctgaggtcaa gttcaactgg       1680
tacgtggacg gcgtggaggt gcataatgcc aagacaaagc cgcgggagga gcagtacaac       1740
agcacgtacc gtgtggtcag cgtcctcacc gtcctgcacc aggactggct gaatggcaag       1800
gagtacaagt gcaaggtctc caacaaagcc ctcccagccc ccatcgagaa aaccatctcc       1860
aaagccaaag gtgggacccg tggggtgcga gggccacatg gacagaggcc ggctcggccc       1920
accctctgcc ctgagagtga ccgctgtacc aacctctgtc cctacagggc agccccgaga       1980
accacaggtg tacaccctgc ccccatcccg ggatgagctg accaagaacc aggtcagcct       2040
gacctgcctg gtcaaaggct tctatcccag cgacatcgcc gtggagtggg agagcaatgg       2100
gcagccggag aacaactaca agaccacgcc tcccgtgctg gactccgacg gctccttctt       2160
cctctacagc aagctcaccg tggacaagag caggtggcag caggggaacg tcttctcatg       2220
ctccgtgatg catgaggctc tgcacaacca ctacacacag aagagcctct ccctgtctcc       2280
gggtaaatga tcccagtgtc cttggagccc tctggtccta caggactctg acacctacct       2340
```

```
ccacccctcc ctgtgtaaat aaagcaccca gcactgcctt gggaccctgc aataatgtcc    2400
tggtgatttc tgagatgtag agtctagcta ggtcatggaa tgaggggtct ccatggtttg    2460
aggcctgagt tgtgactaag gaaaaaccca taggcctaca ctgccacacc cagcactttt    2520
gaatttgcct gacatgaaaa gaattt                                          2546
```

NUCLEIC ACID MOLECULES AND APPLICATIONS THEREOF IN HUMAN ANTIBODY

CROSS REFERENCE TO THE RELATED APPLICATIONS

This application is the national phase entry of International Application No. PCT/CN2018/083163, filed on Apr. 16, 2018, which is based upon and claims priority to Chinese Patent Application No. 201810261091.2, filed on Mar. 27, 2018, the entire contents of which are incorporated herein by reference.

TECHNICAL FIELD

The invention belongs to the field of biotechnology, and more specifically, relates to nucleic acid molecules and their applications thereof.

BACKGROUND

Therapeutic human antibody, also known as a human monoclonal antibody or fully human antibody, is a class of biotechnology products that are currently used to treat the most critical diseases such as tumors, autoimmune diseases, infectious diseases, transplant rejections, etc. Among those therapeutic monoclonal antibodies in the world, seventy-two monoclonal antibodies have been on the market in Europe and the United States, and twenty-seven of them are human antibodies. There are mainly two methods to obtain human therapeutic antibodies. The first method, human antibody is obtained by using a human B⁻cell phage antibody library and deploying phage display technology to mine and improve the antibody affinity; The second method, the a genetically modified (GM) animal is used, specifically, the endogenous immunoglobulin genes of the transgenic animal is inactivated, and then whole (or partial) human immunoglobulin genes are transferred into the animal genome, so a human (or partial) humanized antibodies are produced through animal immune system of the transgenic animal. With the increasingly accumulated research progress on the transgenic technology and transgene in supporting B⁻cell development, the new generation of antibody humanized transgenic animals have become more productive. These transgenic animals have a normal B⁻cell development, and DNA recombination, mutation and antibody maturation, the resulting antibody specificity thereof is extremely high.

Most of the new generation humanized antibody animal lines can only produce human/transgenic host animal chimeric antibodies, that is, the heavy chain variables (V), diversity (D), and joining (J) (VDJ) gene segments of an antibody are derived from human, while the C-region is derived from the transgenic host animal. In the process of antibody drug development, a further humanization process (grafting) is required. This humanization process may change the affinity of the antibody and reduces its druggability. Therefore, it is of very desirable to obtain fully human antibodies directly from the animal in vivo.

In the patent CN105441455A, a human/host animal chimeric IgM sequence is used, which can also produce fully human antibodies. However, there are a few drawbacks: (1) the number of B⁻cells of the transgenic animal is slightly less than that of wild type mice; and (2) the antibody specificity and diversity of the antibody need to be further improved.

SUMMARY

The objectives of the invention are to resolve the above drawbacks in the prior art. Thereof to provide transgenic animal with those nucleic acid molecules can express fully human therapeutic antibodies in vivo, thereby subsequently to reduce the antibody humanization and to increase the druggability of the antibodies.

The objectives of the invention are achieved by the following technical solutions.

Nucleic acid molecules includes immunoglobulin genes or parts of the immunoglobulin genes, characterized in that, the nucleic acid molecule includes IgM gene (IgHCμ) and IgM switch region (Sμ). The sequences of the Sμ and the IgHCμ are both derived from the transgenic host animal.

Further, the IgHCμ includes CH1 exon, CH2 exon, CH3 exon, CH4 exon, and all the intron sequences among them in the IgM locus, and also includes the TM1, TM2, and PolyA signal sequence of the transgenic host animal.

The invention safeguards the development of B⁻cells and the maturation of antibodies in the transgenic host animal.

The above-mentioned nucleic acid molecules further include the IgH heavy chain 5'-enhancer of the transgenic host animal. The structure of the 5'-enhancer with the Sμ and the IgHCμ is shown in FIG. 1-1, and the construction process is shown in FIG. 1.

The above-mentioned nucleic acid molecules further include IgG genes (or Igγ). The IgG genes (C-region) may be from the transgenic host animal and human to form chimeric sequences. The above-mentioned chimeric sequences include Igγ switch region (Sγ), TM1, TM2, the polyA, etc. are derived from the transgenic host animal, and human Igγ CH1 exon, Hinge exon, CH2 exon, CH3 exon, and their introns therebetween to form a transgenic host animal/human chimeric Igγ expression control unit. Specifically, the structure of the Igγ chimeric control region is shown in FIG. 2-1, and the construction process is shown in FIG. 2.

The IgG genes (C-region) may be from human sequences, which include human switch region (Sγ) sequence, human Igγ CH1 exon, human Igγ Hinge exon, human Igγ CH2 exon, human Igγ CH3 exon, human Igγ introns therebetween, human Igγ polyadenylation signal (PolyA), human TM1, human TM2, etc.

The above-mentioned Igγ sequences may include the subtypes of the human and transgenic host animal IgG. This includes Igγ switch regions (Sγ) of each subtype of the human and mouse Igγ. For example, the subtypes of the human Igγ include Igγ3, Igγ1, Igγ2, and/or Igγ4; and the subtypes of mouse Igγ include Igγ3, Igγ1, Igγ2a, and/or Igγ2b.

The above-mentioned nucleic acid molecules further include an IgH 3'-terminal local control region (LCR). The LCR may be derived from the transgenic host animal sequence (see FIG. 6) or the human sequence (see FIG. 5).

The above-mentioned nucleic acid molecules include fully V-regions or modified V-regions of the human IgH heavy chain, D-regions or modified D-regions of the human IgH gene; and J-regions or modified J-regions of the human IgH gene. The heavy chain V-regions, D-regions and J-regions are all derived from humans, as shown in FIGS. 5 and 6.

For example, in detail, the above-mentioned nucleic acid molecules contain part or all human V-regions, the D-regions and the J-regions of the human immunoglobulin heavy chain locus (IgH), and then linked to the mouse immunoglobulin gene (IgH) 5'-enhancer, followed by the mouse switch region (Sµ) sequence, mouse IgM CH1 exon, CH2 exon, CH3 exon, CH4 exon, PolyA, TM1, TM2, etc., then connected to the human Igγ switch region (Sγ) sequence, followed by human Igγ CH1 exon, human Igγ Hinge exon, human Igγ CH2 exon, human Igγ CH3 exon, human PolyA, human TM1, human TM2, etc., finally linked with a human heavy chain IgH 3'-terminal local control region (LCR), as shown in FIG. 5. The transgenic mouse can express mouse IgM and human IgG.

Alternatively, nucleic acid molecules contain part or all human V-regions, the D-regions and the J-regions of the human immunoglobulin locus (IgH), and then linked to the mouse immunoglobulin gene (IgH) 5'-enhancer, followed by the mouse switch region (Sµ) sequence, mouse IgM CH1 exon, CH2 exon, CH3 exon, CH4 exon, PolyA, TM1, TM2, etc., then connected to the mouse Igγ switch region (Sγ) sequence, followed by human Igγ CH1 exon, human Igγ Hinge exon, human Igγ CH2 exon, human Igγ CH3 exon, mouse PolyA, mouse TM1, mouse TM2, etc., finally linked with a mouse heavy chain IgH 3'-local control region (LCR), as shown in FIG. 6. This transgenic mouse can express mouse IgM and human IgG.

A vector contains the above-mentioned nucleic acid molecules.

A prokaryote contains the above-mentioned nucleic acid molecules; A cell contains the above-mentioned nucleic acid molecules or vectors, which include any transgenic cell contains the nucleic acid molecules, and further include but not limited to the lymphocytes, hybridoma cells, antibody-expressing cells, and other cells derived from the transgenic animals.

A human antibody generated from the DNA rearrangement and mutations of the above-mentioned nucleic acid molecules. The human antibody includes any human antibody derived from the above-mentioned nucleic acid molecules or transgenic animals with the above-mentioned nucleic acid molecules. The invention includes but not limited to proteins, DNAs, mRNA, cDNAs, and any antibody (modified or engineered) derived from the nuclei acid molecules and transgenic animal.

A transgenic animal contains the above-mentioned nucleic acid molecules, vector, cells or antibodies. The animal may be pig, cow, horse, mouse, rat, rabbit, chicken, sheep or other mammals.

The invention contains any application of the above-mentioned DNAs, cDNAs and mRNAs, amino acid sequences, proteins, vectors, hybridoma cells, cell lines and transgenic animals.

In particular, the invention provides transgenic animals obtained by transferring the above-mentioned transgenic vectors into animal genome, or the offspring from the cross between the genetically modified animal with another animal with its endogenous immunoglobulin heavy and light chains inactivated, the final transgenic animal can only express human IgG antibodies. Up immunization, this human immunoglobins genetical modified animal can produce antigen-specific fully human IgG antibodies.

A method for making a transgenic animal with the above-mentioned nucleic acid molecules or vectors includes the following steps:
(1) Obtaining the above-mentioned nucleic acid molecules;
(2) Constructing the nucleic acid molecule vectors;
(3) Introducing the vectors into cells (including ES cells, stem cells, induced pluripotent stem cells and somatic cells) or embryos of a transgenic host animal;
(4) Chimeric production or somatic cell cloning with the cells containing the vectors to generate embryos and then transgenic animal; and
(5) Breeding to producing heterozygous and homozygous transgenic animals (including mating with a host animal lacking of endogenous immunoglobulin gene functions).

The above-mentioned host animal with a transgenic vector contain the above-mentioned nucleic acid molecules may be pig, cow, horse, mouse, rat, rabbit, chicken, sheep and other mammals. The above-mentioned vectors include yeast artificial chromosome (YAC), bacterial artificial chromosome (BAC), plasmids, DNA fragment, and others. The method for introducing the above-mentioned vectors into cells or embryos includes electroporation, virus infection, liposome-mediation, microinjection, and others.

For some specific embodiments, the above-mentioned nucleic acid molecules have the sequences as shown in SEQ ID NO:1, SEQ ID NO:2, and SEQ ID NO:3, but this is not intended to limit the scope of the invention. Some non-essential improvements and adjustments to the nucleotide sequences can be made by those skilled in the art, such as deletion, addition, and replacement of some nucleotide sequences.

Advantages
1. The transgenic animal produces various therapeutic human antibodies after the immunization of different antigens.
2. The invention directly obtains human antibodies, which can reduce the laboriously further humanization requirements at the next stage and improves the drug-gability of the antibody.
3. The IgH transgenic animal of the invention uses the IgH 5'-enhancer and IgM sequence of the transgenic host animal itself to ensure the early B⁻cells normal development in the transgenic animal; at the same time, the Igγ of the transgenic animal is also can utilize the switch region (Sγ) sequences and the Igγ polyade-nylation signal (PolyA) and TM1, TM2 sequences of the transgenic host animal to support the expression of human Igγ, which is beneficial to DNA recombination, mutation and BCR (B⁻cell receptor) signal transduction for human Igγ mature under the stimulation of antigen. The IgH construct of transgenic animal have human V-regions, D-regions, J-regions and human Igγ, and human IgK and IgL sequences, so the transgenic animal expresses fully human IgG antibodies.; all transgenic animals prepared with those vectors express the IgG antibody are fully human antibodies, which can reduces the further humanization process in the later period and improves the antibody druggability.
4. The benefits of the invention include: (1) Support normal early B⁻cell development, B⁻cell maturation and B⁻cell number, which are comparable to wild type mouse, resulting standard B⁻cell switch; (2) Expand antibody specificity and diversity; and (3) Improve therapeutic antibody screening efficiency.

BRIEF DESCRIPTION OF THE DRAWINGS

FIGS. 1-6 are key genes in the constructs or vectors of the transgene.

FIG. 13: ELISA ($OD_{450}$) results of transgenic mice after ovalbumin (OVA) immunization.

FIG. 14: Statistical results (Fab amino acid changes and location) of IgH V-region sequence of hybridomas derived from OVA immunized transgenic mice.

FIG. 15: ELISA results (parts) of the hybridoma cell supernatants.

FIG. 16: GPC3 specific antibody binding to HepG2 cells.

FIG. 17: Statistical table of antigen-specific antibodies produced by transgenic mice.

DETAILED DESCRIPTION OF THE EMBODIMENTS

The followings are specific embodiments for describing the invention in detail. It should be pointed out herein that the following embodiments are merely used to further illustrate the invention, and cannot be construed as a limitation to the protection scope of the invention. Some non-essential improvements and adjustments to the invention can be made by those skilled in the art according to the above summary.

Embodiment

The nucleic acid molecules containing those modified human immunoglobulin heavy chains are transferred into mouse genome, and then the transgenic mouse containing the human immunoglobulin genes and endogenous immunoglobulin gene knockouts are immunized to produce human therapeutic antibodies. The simplified steps are as follows.

1. Construction of Immunoglobulin Gene Vectors
1) Construction of Immunoglobulin Heavy Chain Genes (See FIG. 5)

Figure 1:
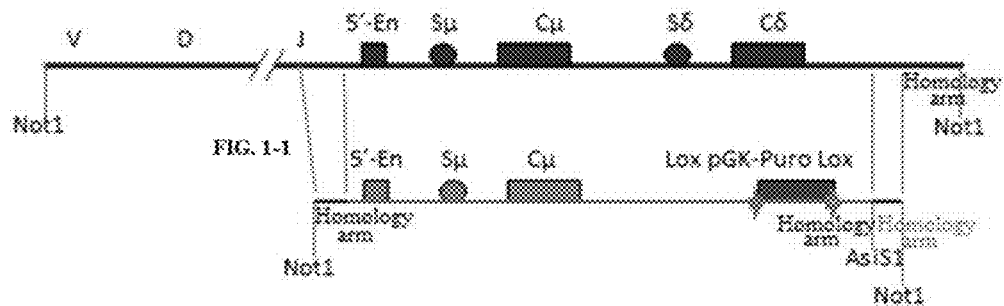
FIG. 1: A schematic diagram of 5'-enhancer and IgM expression construct: The human IgH 5'-enhancer, the human IgM, and the human IgD in a vector are replaced with the mouse 5'-enhancer and the IgM, the homologous arms are used for homologous recombineering (wherein, the homologous arms indicated are used for the homologous recombineering); pGK-Puro is the selection gene for bacteria and mammal transfections, Lox is a specific 34 base pair sequence; and the Not1 and the Asis1 are restriction sites (wherein, the human DNA sequences are shown in dark black color, and the mouse DNA sequences are shown in light black color).
Figure 2:
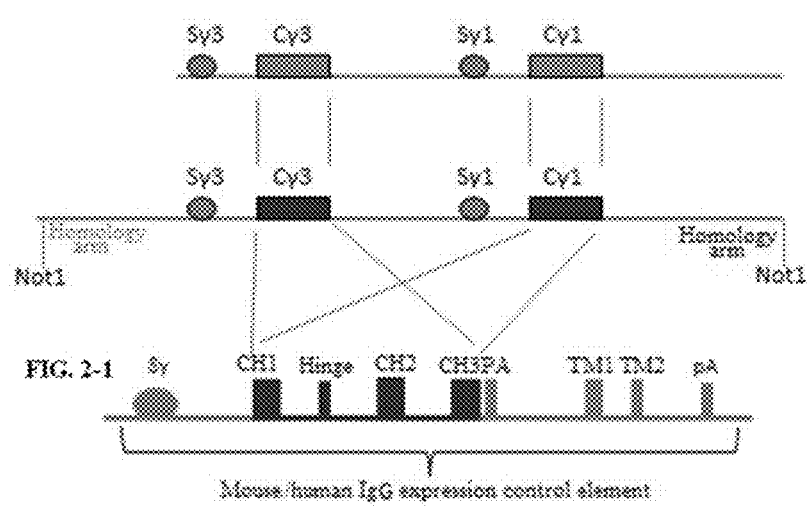
FIG. 2: A schematic diagram of the structure and the construction of the transgenic host animal/human chimeric IgG expression vector: Wherein the homology arms are used for DNA homologous recombineering, the human Cγ CH1, Hinge, CH2 and CH3 sequences is used to replace mouse Cγ CH1, Hinge, CH2 and CH3 sequences by counter-selection recombineering; The Not1 is a restriction site (wherein, the human DNA sequences are shown in dark black color, and the mouse DNA sequences are shown in light black color).
Figure 3:
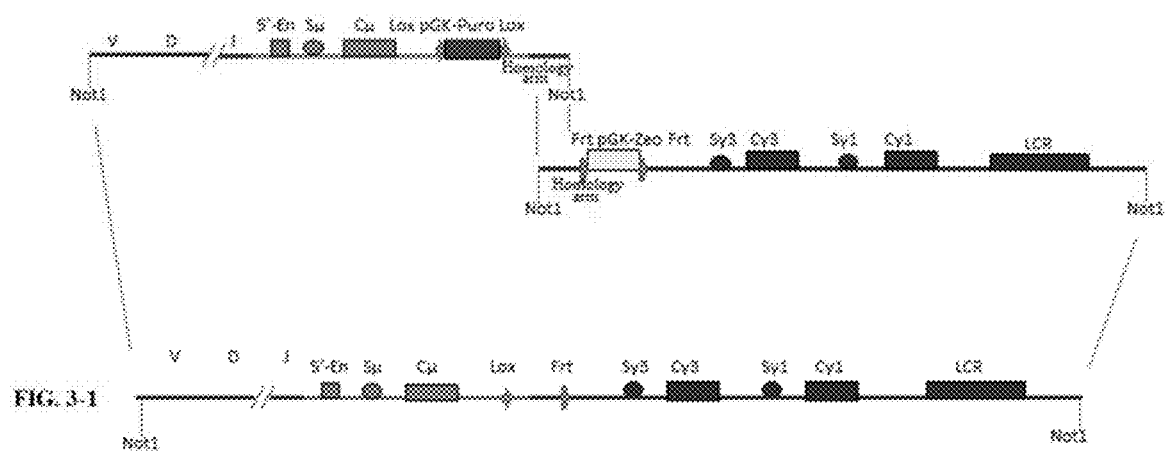
FIG. 3: A schematic diagram of nucleic acid molecules construction of IgG C-region: shows how the mouse 5'-enhancer (5'-En), mouse Sμ, mouse IgM, human Igγ3, human Igγ1 and human 3'-LCR genes are linked together; the puromycin (Puro) and zeocin (Zeo) selection genes are for bacteria and mammalian cell transfections separately; and the Puro and Zeo selection genes can be removed by CRE or Flpo expression plasmid or protein, resulting only one Lox (34 bp) and Frt (34 bp) sequences reminded in the transgene; and this nucleic acid molecule is then linked to the V-regions, the D-regions and the J-regions of the human IgH to generate a transgenic vector (wherein, the human DNA sequences are shown in dark black color, and the mouse DNA sequences are shown in light black color).
Figure 4:
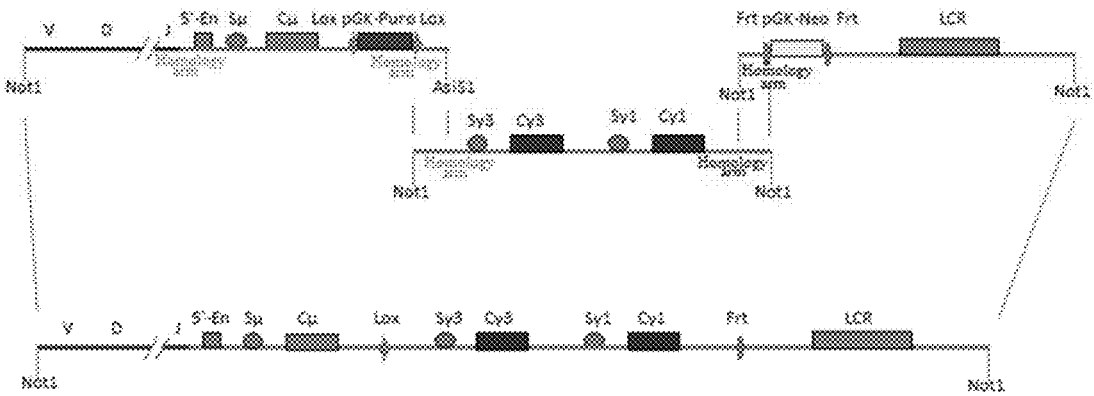
FIG. 4: A schematic diagram of nucleic acid molecules construction of IgG C-region: shows how the mouse 5'-enhancer (5'-En), mouse Sμ, mouse IgM, human/mouse chimeric Igγ3, human/mouse chimeric Igγ1 and mouse 3'-LCR genes are linked together; the puromycin (Puro) and zeocin (Zeo) selection genes are for bacteria and mammalian cell transfections separately; and the Puro and Zeo selection genes can be removed by CRE or Flpo expression plasmid or protein, resulting only one Lox (34 bp) and Frt (34 bp) sequences reminded in the transgene; and this nucleic acid molecule is linked to the V-regions, the D-regions and the J-regions of the human IgH to generate a transgenic vector (wherein, the human DNA sequences are shown in dark black color, and the mouse DNA sequences are shown in light black color).

First, the mouse IgM 5'-enhancer and all the expression and control sequences of IgM, homology arms and selection genes are obtained by PCR and gene synthesis (see FIG. 1). Subsequently, the human Igγ3, Igγ1 and 3'-LCR sequences, homology arms and selection genes are also generated (see FIG. 3). Next, all DNA fragments are linked accordingly by homologous recombineering to produce new DNA vectors, and then the above-mentioned modified DNA vectors are transferred into YAC vector or BAC vector, which contains the human immunoglobulin heavy chain (Ig). Finally, the transgenic vectors of the modified immunoglobulin heavy chain is constructed as showed in FIG. 5 (wherein, the vector sequences are confirmed by PCR and sequencing, wherein, the human DNA sequences are shown in dark black color, and the mouse DNA sequences are shown in light black color). The vector successively includes V-regions, D-regions and J-regions of the human immunoglobulin heavy chain locus, mouse IgH 5'-enhancer, mouse IgM, human Igγ3, human Igγ 1, and human 3'-LCR.

Figure 6:
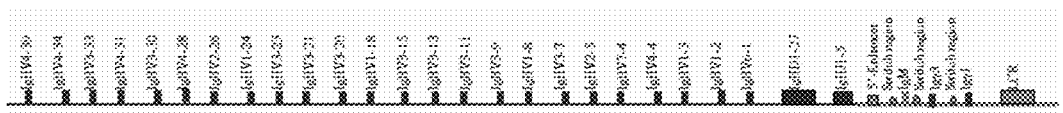
FIG. 6: A vector of IgH heavy chain of a transgenic nucleic acid molecule: wherein the transgenic vector contains the human V-regions, D-regions and J-regions of the human IgH, the mouse IgH 5'-enhancer, the mouse IgM switch region (Sμ) sequence, and all exon sequences and regulatory elements of the mouse IgM, further contains the mouse Igγ3 switch region (Sγ3) sequence, CH1, Hinge, CH2, CH3 sequences of the human Igγ3, PolyA, TM1, TM2, etc. of the mouse Igγ3, and contains the mouse Igγ1 switch region (Sγ1) sequence, the CH1, Hinge, CH2 and CH3 sequences of the human Igγ1, and the PolyA, TM1, TM2 and el al of the mouse Igγ1, and then links to the mouse IgH 3'-local control region (LCR) (wherein, the human DNA sequences are shown in dark black color, and the mouse DNA sequences are shown in light black color).

2) Construction of Immunoglobulin Heavy Chain Genes (See FIG. 6)

First, the mouse IgM 5'-enhancer and all the expression and control sequences of IgM, homology arms and selection genes are obtained by PCR and gene synthesis (as above, see FIG. 1). Subsequently, the mouse Igγ3 CH1, Hinge, CH2 and CH3 is replaced by human Igγ3 CH1, Hinge, CH2, CH3 sequences; the mouse Igγ1 CH1, Hinge, CH2 and CH3 is replaced by human Igγ1 CH1, Hinge, CH2, CH3 sequences through homologous arms by homologous recombineering and counter-selection recombineering, then linked to mouse 3'-LCR sequences (see FIG. 3). Finally, the transgenic vectors of the modified immunoglobulin heavy chain are constructed as showed in FIG. 6 (wherein, the vector sequences are confirmed by PCR and sequencing, wherein, the human DNA sequences are shown in dark black color, and the mouse DNA sequences are shown in light black color). The vector successively includes V-regions, D-regions and J-regions of the human immunoglobulin heavy chain locus, mouse IgH 5'-enhancer, mouse IgM, mouse/human chimeric Igγ3 and mouse/human chimeric Igγ1 expression unit, and mouse 3'-LCR.

2. Generations of Human Antibody Transgenic Mouse

1) Generation of Transgenic Mice with Human Immunoglobulin Heavy Chain

A. Creation of Transgenic Mouse with Human Immunoglobulin Heavy Chain (Antibody Transgenic Mouse HGa)

The human immunoglobulin heavy chain vector mentioned in above 1) (see FIG. 5) of Method 1 is transferred into mouse genome by conventional transgenic technique. The transgenic mouse (HGa) with integrated fully human immunoglobulin heavy chain is confirmed by both PCR and ELISA analysis.

Figure 8:
FIG. 8: PCR results of human IgHV2-26 from transgenic mice (HGa).
Figure 9:
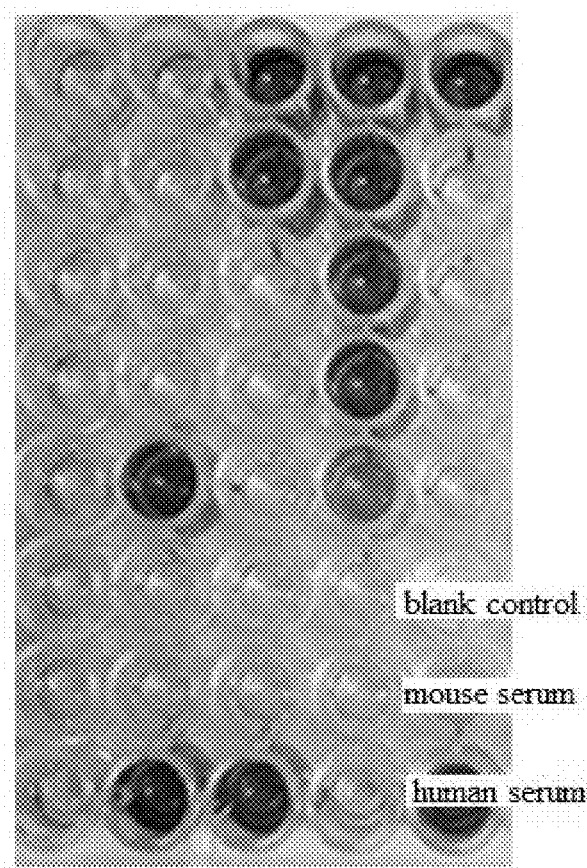
FIG. 9: Serum ELISA results of transgenic mice (HGa).

The PCR reactions are as follows.
Human IgHV2-26 PCR:
  Primer sequences: SEQ ID NO.4 and SEQ ID NO.5.
  The size of the PCR product: 433 bp.
  The PCR results are shown in FIG. 8. Note: the genomic DNA PCR results of the human IgHV2-26 transgenic mouse show that the positive mice have a PCR band of 433 bp in size (1% gel electrophoresis).
  Human Igγ1 PCR:
  Primer sequences: SEQ ID NO.6 and SEQ ID NO.7.
  The size of the PCR product: 417 bp.
  ELISA analysis of transgenic mice: human serum and wild type mouse serum are used as controls, see FIG. 9. Note: the human IgG in transgenic mouse serum is detected by Elisa at a 1:100 dilution. The transgenic mice are positive for human IgG in parallel with the human serum, the wild type mouse serum and blank control. The antibodies used for the ELISA detection are: Goat Anti Human IgG Fc (ab97221, Abcam) and Goat Anti-Human IgG Fc (HRP) (ab97225, Abcam).

B. Creation of Transgenic Mice with Human Immunoglobulin Heavy Chain Gene (Antibody Transgenic Mouse HGb)

The human immunoglobulin heavy chain vector mentioned in above 2) (see FIG. 6) of Method 1 is transferred into mouse genome by conventional transgenic technique. The transgenic mouse (HGa) with integrated fully human immunoglobulin heavy chain is confirmed by both PCR and ELISA analysis.

Figure 10:
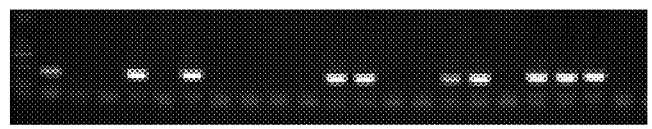
FIG. 10: PCR results of human IgHV2-26 from transgenic mice (HGb).
Figure 11:
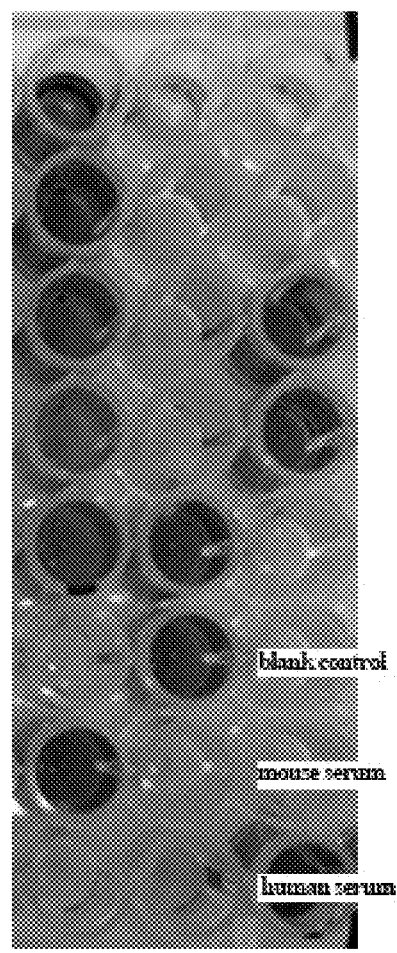
FIG. 11: Serum ELISA results of transgenic mice (HGb).

The PCR reactions are as follows.
Human IgHV2-26 PCR:
  Primer sequences: SEQ ID NO.4 and SEQ ID NO.5.
  The size of the PCR product: 433 bp.
  The PCR results are shown in FIG. 10. Note: the genomic DNA PCR results of the human IgHV2-26 transgenic mouse show that the positive mice have a PCR band of 433 bp in size (1% gel electrophoresis).
  Human Igγ1 PCR:
  Primer sequences: SEQ ID NO.6 and SEQ ID NO.7.
  The size of the PCR product: 417 bp.
  ELISA analysis of transgenic mice: human serum and wild type mouse serum are used as controls, see FIG. 11. Note: the human IgG in transgenic mouse serum is detected by Elisa at a 1:100 dilution. The transgenic mice are positive for human IgG in parallel with the human serum, the wild type mouse serum and blank control. The antibodies used for the ELISA detection are: Goat Anti Human IgG Fc (ab97221, Abcam) and Goat Anti-Human IgG Fc (HRP)

Figure 7:
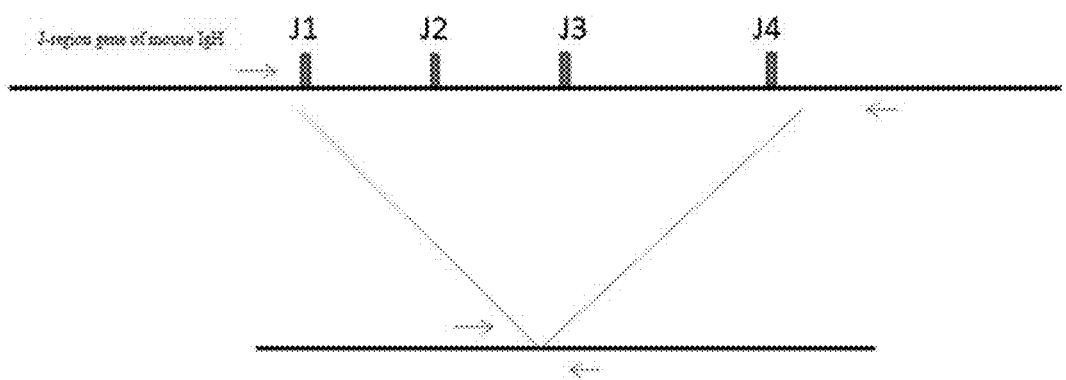
FIG. 7: Mouse IgH immunoglobulin heavy chain J-region gene target: Wherein the J-regions of the mouse IgH is composed of J1, J2, J3, and J4 exons, and the whole J-region sequence is deleted by the gene targeting; Homogenous mice without the J-region sequences cannot produce any mouse-derived Ig (including IgM and IgG).

2) Creation of Immunoglobulin Heavy Chain Gene Knockout Mice (mH⁻Mice, See FIG. 7)

Immunoglobulin heavy chain gene knockout mice are constructed by a gene targeting technique. The IgH J-region of the mouse immunoglobulin heavy chain gene is selected as the gene knockout site (see FIG. 6 for the gene knockout site and gene knockout effect), and then the immunoglobulin heavy chain gene knockout mice are obtained. The transgenic mouse (mH⁻) with immunoglobulin heavy chain gene knockout is confirmed by both PCR and ELISA analysis.

The primers used for the IgH-JH PCR identification are as follows:
  Primer sequences: SEQ ID NO.8; SEQ ID NO.9.
  PCR products: the size of the PCR product of the JH-region after the gene targeting is 732 bp, while the size of the PCR product of the wild type JH-region is 2422 bp.

3) Production of Immunoglobulin Kappa Light Chain Knockout Mouse (mIC⁻⁻ Mouse, CN105441455A patent)

4) Production of Transgenic Mouse with a Human Immunoglobulin Kappa Light Chain Locus (HK⁺ Mice, CN105441455A patent)

5) Production of Transgenic Mice with a Human Immunoglobulin Lambda Light Chain Locus (HL⁺ Mice, CN105441455A patent)

6) Breeding to Generate Humanized Antibody Transgenic Mouse

The transgenic mouse HGa or transgenic mouse HGb obtained in 2 of the method are crossed with the mice obtained in 2), 3), 4) and 5) of the method respectively. After PCR and ELISA analysis, five-feature transgenic mice (HGa⁺HK⁺HL⁺mK⁻⁻mH⁻⁻ and HGb⁺HK⁺HL⁺mK⁻⁻mH⁻⁻) with high expression of human IgG antibodies without (or low) mouse endogenous immunoglobulin IgL are finally obtained.

Figure 5:
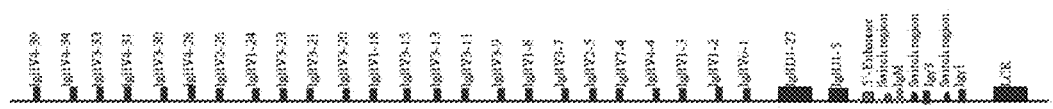
FIG. 5: A vector of IgH heavy chain of a transgenic nucleic acid molecule: wherein the transgenic vector contains the human V-regions, D-regions and J-regions of the human IgH, the mouse IgH 5'-enhancer, the mouse IgM switch region (Sμ) sequence, and all exon sequences and regulatory elements of the mouse IgM, further contains the human Igγ3 switch region (Sγ3) sequence, CH1, Hinge, CH2, CH3 sequences of the human Igγ3, PolyA, TM1, TM2, etc. of the human Igγ3, and contains the human Igγ1 switch region (Sγ1) sequence, the CH1, Hinge, CH2 and CH3 sequences of the human Igγ1, PolyA, TM1, TM2, etc. of the human Igγ1, and then links to the human IgH 3'-local control region (LCR) (wherein, the human DNA sequences are shown in dark black color, and the mouse DNA sequences are shown in light black color).

Characterizations of Transgenic Mice:

A. ELISA Results of the Serum IgM and IgG Level of the Five-Feature Transgenic Mice:

Results: The serum IgM level of wild type mouse is 0.8-6.5 mg/mL;

The serum IgM level of the transgenic mouse (HGa⁺HK⁺ HL⁺mK⁻⁻mH⁻⁻, transgenic IgH heavy chain vector is shown in FIG. 5) is 0.1-2.8 mg/mL;

The serum IgM level of the transgenic mouse (HGb+HK+HL+mK−−mH−−, transgenic IgH heavy chain vector is shown in FIG. 6) is 0.4-2.5 mg/mL;

The serum IgG level of human is 3.5-15 mg/mL;

The serum human IgG level of the transgenic mouse (HGa+HK+HL+mK−−mH−−, transgenic IgH heavy chain vector is shown in FIG. 5) is 0.08-1.2 mg/mL; and The serum human IgG level of the transgenic mouse (HGb+HK+HL+mK−−mH−−, transgenic IgH heavy chain vector is shown in FIG. 6) is 0.5-2.5 mg/mL.

The serum level of the mouse IgM and human IgG of the transgenic mice are a little lower than that of the human, because the transgenic mice are kept in a clean and IVC caged environment.

B. Serum Human IgG Titer of Transgenic Antibody Mice (in Compared with the Transgenic Mice from CN10544145A patent), See FIG. 12.

Figure 12:
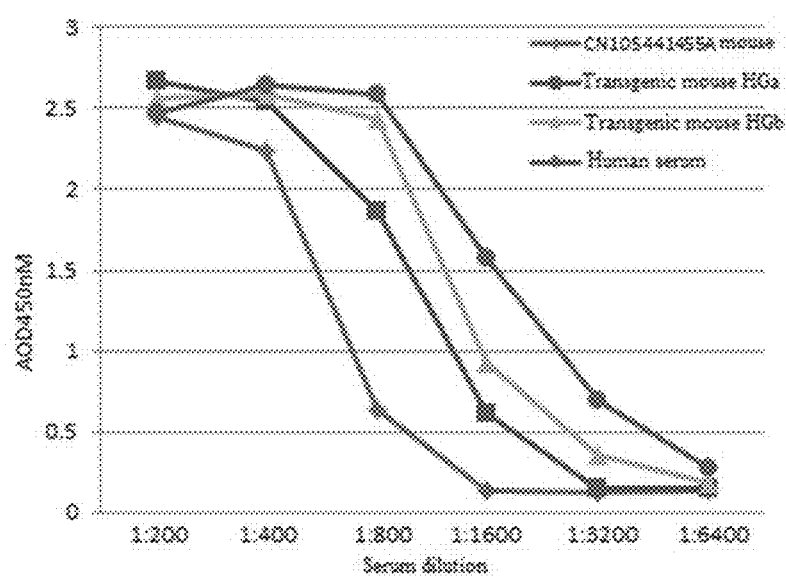
FIG. 12: Human serum IgG titer of transgenic antibody mice (at different dilution conditions).

Notes: the ELISA results show in FIG. 12 that the serum human IgG titer of the transgenic antibody mice at this invention including HGa$^+$HK$^+$HL$^+$mK$^{--}$mH$^{--}$ (HGa five feature transgenic mouse), HGb$^+$HK$^+$HL$^+$mK$^{--}$mH$^{--}$ (HGb five feature transgenic mouse) and HG$^+$HK$^+$HL$^+$mK$^{--}$mH$^{--}$ (HG five feature transgenic mouse, CN10544145A), and the serum samples is diluted at 1:10, 1:100, 1:1000, 1:10000, 1:100000, and 1:1000000, respectively (an average value of 3-5 five-feature transgenic mice).

3. Generation of Fully Human Antibodies

The fully human antibody transgenic mice are immunized to produce specific B−cells, and then combining with hybridoma and cell culture techniques to produce therapeutic human antibodies.

OVA Immunization and Antibody Production 2) 8-Week-Old Humanized Antibody Transgenic Mice are Selected for the Immunization with OVA.

Primary Immunization:
- (1a) OVA (Sigma A7641) antigen is diluted with PBS to a final concentration of 2 mg/mL, then 20 μg of CpG (ODN1826, tlrl-1826, Invivogen) is added, and then an appropriate amount of aluminum hydroxide (vac-alu-50, Invivogen) is added to allow a concentration of the aluminum hydroxide to be 1%.
- (2a) 0.75 mL of the antigen prepared in step (1a) is mixed with a complete Freund's adjuvant (CFA, Sigma F5881) in a ratio of 1:1, and emulsified with a MIX-PAC™ syringe. Each mouse is immunized by subcutaneous injection at a dose of 200 μL each (0.2 mg).

Secondary Immunization:
- (1b) On the 21$^{st}$ day after the primary immunization, a secondary immunization is performed. The antigen is diluted with PBS to a final concentration of 1.0 mg/mL, then 10 μg of CpG is added, and an appropriate amount of aluminum hydroxide is added to allow a concentration of the aluminum hydroxide to be 1%.
- (2b) 0.75 mL of the antigen prepared in step (1b) is mixed with an incomplete Freund's adjuvant (IFA) in a ratio of 1:1, and emulsified with a MIXPAC™ syringe. Each mouse is immunized by intraperitoneal injection at a dose of 200 μL (0.1 mg).

Third Immunization:
- (1c) On the 21$^{st}$ day after the secondary immunization, a 3$^{rd}$ immunization is performed. The antigen is diluted with PBS to a final concentration of 1.0 mg/mL, then 10 μg of CpG is added, and an appropriate amount of aluminum hydroxide is added to allow a concentration of the aluminum hydroxide to be 1%.
- (2c) The antigen protein prepared according to the method in step (1c) is injected directly. Each mouse is immunized by intraperitoneal injection at a dose of 200 μL (0.1 mg).

Fourth Immunization:
- (1d) On the 21$^{st}$ day after the 3$^{rd}$ immunization, a 4$^{th}$ immunization is performed. The antigen is diluted with PBS to a final concentration of 1.0 mg/mL, then 10 μg of CpG is added, and an appropriate amount of aluminum hydroxide is added to allow a concentration of the aluminum hydroxide to be 1%.
- (2d) The antigen protein prepared according to the method in step (1d) is injected directly. Each mouse is immunized by intraperitoneal injection at a dose of 200 μL (0.1 mg).

Booster Immunization:

On the 21$^{st}$ day after the 4$^{th}$ immunization, mice with satisfactory serum ELISA human IgG titer are given a booster immunization, and then splenic B−cells are obtained for hybridoma fusion, culture and screening.

2) Mouse Serum Enzyme-Linked Immunosorbent Assay (ELISA)

On the 10$^{th}$ day after the 4$^{th}$ immunization, the blood of the mice is taken for ELISA analysis, and the human IgG titer of the immunized mouse serum is investigated, with the pre-immunized mice as the control. The results are as follows.

Detection of human IgG titer in mouse serum: 96-well plates are embedded with an antigen OVA, and the specific anti-human IgG-HRP antibody (Millipore, AP113P) at a dilution of 1:8000 is used. The serum of wild type Kunming white mouse is as control for mouse IgG.

The results show that the transgenic antibody mice have a great human IgG titer in the transgenic mouse serum after immunization. The transgenic mouse with OD$_{450}$>1 human IgG titer at serum dilution of 1:8000 are selected for hybridoma fusion.

The ELISA (OD$_{450}$) results of the mice (HGa$^+$HK$^+$HL$^+$mK$^{--}$mH$^{--}$ and HGb$^+$HK$^+$HL$^+$mK$^{--}$mH$^{--}$) after immunization with OVA are shown in FIG. 13. Notes: HGa transgenic mice are HGa$^+$HK$^+$HL$^+$mK$^{--}$mH$^{--}$ five-feature transgenic mice; HGb transgenic mice are HGb$^+$HK$^+$HL$^+$mK$^{--}$mH$^{--}$ five-feature transgenic mice; and wild type Kunming white mice are normal control. After the mice are immunized with OVA for 4$^{th}$ immunizations, anti-OVA specific human IgG antibody titer in their serum (different dilution concentrations) are detected by ELISA.

The statistical results (Fab amino acid number and location of mutations) of the antibody IgG V-region amino acid sequence from the OVA-immunized mice are shown in FIG. 14.

3) Generation of Human Antibodies

GPC3 Immunization and Antibody Production

The transgenic mice (HGb$^+$HK$^+$HL$^+$mK$^{--}$mH$^{--}$) are immunized with GPC3 peptide, and the splenic cells of the mice are collected and fused with Sp2/0 cells to obtain monoclonal antibodies, the fully human therapeutic antibodies.

After immunizations with antigen, the transgenic animals are used for hybridoma fusion. The selection is carried out in a semi-solid medium, and next, hybridoma clones are picked into 96-well plates and cultured further. Subsequently, the hybridoma supernatants are analyzed for specific antibodies by ELISA.

The ELISA results from two of 96-well plates of the hybridoma supernatants are shown in FIG. 15 (in the ELISA results of two hybridoma 96-well plates after performing hybridoma fusion and selections on solid medium, the anti-GPC3 fully human antibody is showed in the lighter colored wells, after a GPC3 peptide immunization) (the 96-well plates are embedded with the antigen, then the hybridoma supernatants are added onto the 96-well plates. After that, the human IgG-HRP antibody and 3,3',5,5'-tetramethylbenzidine (TMB) are added for color development).

The GPC3 positive cell line HepG2 are used to analyses the antibodies (4-10F-4G and 6-7A-2E) generated from the transgenic mouse (as shown in FIG. 16), the results prove that 4-10F-4G has no function, while 6-7A-2E can specifically bind to the HepG2 cells, indicating that the transgenic antibody mice can produce antigen-specific anti-GPC3 antibodies (6-7A-2E).

The affinities of the antibodies from B⁻cell hybridoma supernatants obtained after the HGa and HGb transgenic mice immunized with OVA protein, GPC3 protein and GPC3 peptides are list in FIG. 17. Transgenic mouse lines (HGa and HGb) both can generate antigen-specific antibodies with high affinities after GPC3 polypeptide and GPC3 protein immunizations.

(1) The size of the spleen of the transgenic mice obtained of the invention is similar to that of the wild type mice, and is larger than that of the transgenic mice of CN105441455A.
(2) The B⁻cell number in bone marrow and spleen of the transgenic mice of the invention has more B⁻cells number than that of the transgenic mice of CN105441455A.
(3) The transgenic mice of the invention have a higher percentage of IgM cells than that of the transgenic mice of CN105441455A.
(4) The transgenic mice of the invention have a higher percentage of IgG cells than that of the IgG cells of transgenic mice of CN105441455A, housed in the same clean and IVC caged environment.
(5) There are more changes in the antibody complementarity-determining regions (CDR) of the transgenic IgH heavy chain of the invention: Under the same antigen immunization conditions, the V-sequence mutations of the human IgG antibody of the transgenic mice of the invention are more than that of the transgenic mice of CN105441455A.

The numbers of B⁻cells in the spleens of the transgenic mice HGa⁺HK⁺HL⁺mK⁻⁻mH⁻⁻ after the immunization are $6.2 \times 10^7$, $1.0 \times 10^8$, and $9.5 \times 10^7$, respectively.

The numbers of B⁻cells in the spleens of the transgenic mice HGb⁺HK⁺HL⁺mK⁻⁻mH⁻⁻ after the immunization are $1.2 \times 10^8$, $1.02 \times 10^8$, and $1.25 \times 10^8$, respectively.

The numbers of B⁻cells in the spleens of the wild type mice after the immunization are $1.5 \times 10^8$, $1.8 \times 10^8$, and $1.9 \times 10^8$, respectively.

Figure 18:
FIG. 18: Size of the spleens of transgenic mice [A. transgenic mouse (HGa), B. transgenic mouse (HGb), and C. wild type mouse].

The spleens of the transgenic mice after the immunization are shown in FIG. 18: FIG. 18-A is a photograph of the spleen of the transgenic mouse HGa⁺HK⁺HL⁺mK⁻⁻mH⁻⁻ after the immunization; FIG. 18-B is a photograph of the spleen of the transgenic mouse HGb⁺HK⁺HL⁺mK⁻⁻mH⁻⁻ after the immunization; and FIG. 18-C is a photograph of the spleen of the wild type mouse after the immunization.

What is claimed is:

1. Nucleic acid molecules comprising immunoglobulin genes or parts of the immunoglobulin genes, wherein the nucleic acid molecules comprise:
   - an IgH heavy chain 5'-enhancer,
   - an IgM gene comprising IgHCµ and an IgM switch region comprising Sµ derived from a transgenic host animal, wherein the transgenic host animal is a mouse; and
   - further comprising IgG genes (Igγ), wherein the IgG genes are transgenic host animal/human chimeric sequences comprising human subtypes Igγ3, Igγ1, Igγ2, and Igγ4 and mouse subtypes Igγ3, Igγ1, Igγ2a and Igγ2b.

2. The nucleic acid molecules according to claim 1, comprising a human IgH heavy chain 3'-local control region or a transgenic host animal IgH heavy chain 3'-local control region.

3. The nucleic acid molecules according to claim 1, comprising all or parts of V-regions of human IgH heavy chain, all or parts of D-regions of human IgH, and all or parts of J-regions of human IgH.

4. A vector, containing the nucleic acid molecules according to claim 1.

5. The nucleic acid molecules according to claim 1, wherein a nucleotide sequence of the Sµ is positions 2550 to 4451 in SEQ ID NO: 1.

6. The nucleic acid molecules according to claim 1, wherein a nucleotide sequence of the IgH heavy chain 5'-enhancer is positions 433 to 1444 in SEQ ID NO: 1.

7. The nucleic acid molecules according to claim 1, wherein the nucleic acid molecules further comprise Sγ switch regions between the Igγ subtypes.

* * * * *